United States Patent [19]

Albert et al.

[11] 4,197,112
[45] Apr. 8, 1980

[54] WATER-DISPERSIBLE HERBICIDE COMPOSITIONS

[75] Inventors: Robert E. Albert; James D. Metzger, both of Wilmington, Del.

[73] Assignee: E. I. Du Pont de Nemours and Company, Wilmington, Del.

[21] Appl. No.: 938,631

[22] Filed: Sep. 7, 1978

Related U.S. Application Data

[63] Continuation-in-part of Ser. No. 841,450, Oct. 12, 1977, abandoned.

[51] Int. Cl.$^2$ .................. A01N 9/22; C07D 251/46
[52] U.S. Cl. .................. 71/93; 544/211; 71/DIG. 1
[58] Field of Search .......... 71/93, DIG. 1; 544/211

[56] References Cited

U.S. PATENT DOCUMENTS

| | | | |
|---|---|---|---|
| 2,044,942 | 6/1936 | Heckert | 23/122 |
| 2,635,055 | 4/1953 | Figdor | 106/271 |
| 3,248,182 | 4/1966 | Herink et al. | 23/300 |
| 3,585,230 | 6/1971 | Woylheshin | 260/453 |
| 3,762,925 | 10/1973 | Nittel | 96/100 |
| 3,902,887 | 9/1975 | Lin | 71/93 |
| 3,932,224 | 1/1976 | Hirota | 203/7 |
| 3,943,059 | 3/1976 | Chiu | 252/8.55 D |
| 3,979,317 | 9/1976 | Angelini | 252/170 |
| 3,989,452 | 11/1976 | Hugelshofer | 8/42 R |

FOREIGN PATENT DOCUMENTS 1290351   9/1972   United Kingdom .

OTHER PUBLICATIONS

Boullet, Chem. Abst., vol. 30, (1936), 3696a.
Milone et al., Chem. Abstr., vol. 42, (1948), 2832d.
Truffaut et al., Chem Abst., vol. 47, (1953), 4034b.
Kotylar, Chem. Abst., vol. 78, (1973), 86283q.

Primary Examiner—Catherine L. Mills

[57] ABSTRACT

A water-dispersible triazine herbicide composition, having improved crystallization characteristics when dispersed in water below about 37° C. at concentrations above the solubility limits of the triazine, consisting essentially of (a) 1-methyl-3-cyclohexyl-6-dimethylamino-s-triazine-2,4(1H,3H)-dione, and (b) at least about 2% by weight, basis dry triazine, of a surfactant selected from the group consisting of isopropyl naphthalene sulfonic acid and alkali metal or alkaline earth metal salts thereof.

12 Claims, No Drawings

WATER-DISPERSIBLE HERBICIDE COMPOSITIONS

CROSS REFERENCE TO RELATED APPLICATION

This application is a continuation-in-part of copending application Ser. No. 841,450, filed Oct. 12, 1977, now abandoned.

FIELD OF THE INVENTION

The invention relates to a water-dispersible herbicide composition which can be applied by spraying. In particular, it relates to such compositions which can be applied at high concentrations without incurring plugging of the spray nozzle.

BACKGROUND OF THE INVENTION

It is customary to formulate herbicides as water-dispersible compositions which can be readily mixed with water and applied by means of spraying apparatus. An important class of herbicides which can be applied by this means comprises the symmetrical triazine diones, of which 1-methyl-3-cyclohexyl-6-dimethylamino-s-triazine-2,4(1H,3H)-dione is the most widely used. Formulations of this herbicide are marketed throughout the world under the trade name Velpar ® weed-killing compounds (trademark of E. I. du Pont de Nemours and Company, Wilmington, Delaware).

One difficulty with many herbicide formulations is that the active ingredient has limited solubility in the water in which it is dispersed under the conditions of temperature at which the spraying is carried out. Heretofore, this has meant that the spray concentrations of many herbicides had to be limited to below its solubility limit in order to avoid crystallization within the spray apparatus and concomitant plugging of the spray nozzle. Nozzle plugging is most likely to take place when a crystal size of 150μ in any dimension is reached. Such plugging is of significant economic detriment for the reasons that (1) manpower time must be expended to discontinue spraying operations and remove the plugging material and (2) any area sprayed before the plugging is detected and corrected is likely to be covered inadequately. Thus, there is considerable practical need for spraying systems which have reduced plugging tendencies, which, nevertheless, can be used at relatively high concentrations.

The important symmetrical triazine dione, 1-methyl-3-cyclohexyl-6-dimethylamino-s-triazine-2,4-(1H,3H)-dione, is one of those compounds which, because of its limited solubility in water, frequently incurs plugging when used at concentrations above its solubility limit at temperatures below about 37° C. (98.6° F.). For this reason, liquid spray compositions containing Velpar ® herbicidal compounds have been limited to concentrations of about 2-3% by weight active triazine compounds, unless they are heated to raise the solubility limit.

BRIEF DESCRIPTION OF THE INVENTION

The invention is, therefore, directed to a water-dispersible herbicide composition consisting essentially of (a) 1-methyl-3-cyclohexyl-6-dimethylamino-s-triazine-2,4(1H,3H)-dione and (b) a surfactant selected from the group consisting of isopropyl naphthalene sulfonic acid and the alkali metal or alkaline earth metal salts thereof in sufficient amount to improve the crystallization characteristics of the triazine component.

DETAILED DESCRIPTION OF THE INVENTION

The primary herbicide component of the composition of the invention is the above-referred triazine dione. However, it may be used in conjunction with other herbicides or compounds having desired biological activity so long as the other active material does not itself incur plugging problems under the conditions of use. Thus, the triazine dione herbicide can be used with other herbicides such as diuron, terbacil and atrazine.

In most instances, it will be preferred to formulate the active herbicide ingredient in the conventional manner, depending upon the manner of formulation. Such formulating additives include wetting agents, dispersing agents, binders, antiflocculating agents, anticaking agents, fillers, diluents and the like.

In formulating the composition of the invention, the surfactant component also serves as a wetting agent. Thus, the amount of wetting agent which would usually be required can ordinarily be reduced by the amount of the above-referred isopropyl naphthalene sulfonate surfactant.

The minimum amount of active surfactant relative to the triazine dione is quite important and must be at least about 2% by weight, and is preferably at least about 5% weight, basis dry triazine compound, in order to obtain effective modification of the crystallization characteristics of the triazine compound. The upper limit is not, however, critical so long as it does not interfere with the rheology of the system. However, no more than about 10% by weight, basis dry triazine compound, is needed to obtain adequate crystal modification. Additional quantities may, nevertheless, be used to obtain further wetting without detriment to the crystallization characteristics of the composition. The minimum effective amount of a given surfactant material will, of course, be increased by the inclusion therein of inert materials such as diluents and fillers.

Within the above limitation as to the amount of sulfonate surfactant relative to the triazine diones, the composition of the invention can be formulated in the conventional manner. These include concentrated particulate formulations in the form of dusts, granules, pellets, and wettable powders. The triazine compound can be formulated before, during or after addition of the sulfonate surfactant. For example, the composition may comprise finely divided particles of the triazine and the sulfonate in admixture or the sulfonate can be incorporated either within or coated on the triazine particles.

Likewise, the composition of the invention can be formulated as flowable suspensions or solutions in which the triazine is dispersed or dissolved in an aqueous solution of the sulfonate surfactant. High strength compositions are primarily used as intermediates for further formulation or dilution in water for spraying. The formulations, broadly, contain about 1% to 99% by weight of active ingredient(s) and at least one of (a) about 0.1% to 20% surfactant(s) and (b) about 1% to 99% solid or liquid diluent(s). More specifically, they will usually contain these ingredients in the following approximate proportions:

| | PERCENT BY WEIGHT, DRY BASIS | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules & Pellets | 1–95 | 5–99 | 0–15 |
| High Strength Compositions | 90–99 | 0–10 | 0–6 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Co., Ridgewood, N.J., as well as Sisely and Wood, "Encyclopedia of Surface Active Agents", Chemical Publ. Co., Inc., New York, 1964, lists surfactants and recommended uses. All formulations contain minor amounts of additives to reduce foam, caking, corrosion, microbiological growth, etc. Preferably, ingredients should be approved by the U.S. Environmental Protection Agency for the use intended.

The methods of making such formulations are well known. Solutions are prepared by simply mixing the ingredients. Fine solid compositions are made by blending, and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques.

While the compositions of the invention are fully operable for their intended use as herbicides above 37° C., in fact they have no advantage at such higher temperature since the problem of formation of large crystals of the triazine dione compound does not occur unless the compound is present at a concentration above its solubility limit at temperatures below about 37° C. Thus, the composition of the invention is not needed if the spraying medium is heated to above that temperature.

A unique aspect of the invention is the compositional criticality of the sulfonate surfactant. While many surfactants of widely varying compositions have been tested, the only ones which have been found to be operable for the purpose of the invention, i.e. to inhibit the growth of large crystals of the triazine dione herbicides, are members of the quite narrow class consisting of isopropyl naphthalene sulfonic acid and the alkali metal or alkaline earth metal salts thereof.

The isopropyl naphthalene sulfonic acid surfactants which will ordinarily be used for the invention are commercially available as complex mixtures, which vary somewhat in composition depending on their source. A typical sulfonate of this kind will contain mono-, di-, tri- and perhaps even some polyisopropyl-substitution in the various possible naphthalene ring positions. Such surfactants having an average of about 2.5 isopropyl groups per molecule of naphthalene sulfonate molecule have been found to be especially suitable.

Especially in view of the quite surprising compositional criticality of the surfactant, the mechanism by which it functions is not known with certainty. However, it is feasible that as new crystal surfaces are generated, the surfactant interferes with the formation of any larger crystalline surfaces. Another possibility is that the sulfonate surfactant interacts with the crystal matrix itself. That is, as the crystal grows, the sulfonate interferes with matrix formation by either fitting into the matrix and stopping it or by surrounding the crystal and isolating it from further growth.

In general, the compositions of the invention are applied at the rate of 2–12 lbs. per acre, basis dry formulation, in sufficient water to disperse the formulated composition. Of interest in this regard is that it has been determined that the composition of the invention is not unduly sensitive to normal variation in pH or water hardness. Thus, any available water source otherwise suitable for agricultural use can be used to dilute the composite of this invention for spraying.

The examples which follow illustrate both the problem presented by ordinary triazine formulations and the solution thereto which is given by the compositions of the invention.

TEST PROCEDURE

The following described test was devised to measure the plugging tendency of herbicide spray compositions by measuring the amount of crystals formed under specified test conditions.

The test is performed by admixing a measured amount of the herbicide formulation with a measured amount of water at different temperatures with controlled stirring both as to time and shear rate. At the end of the mixing time, the aqueous composition is poured onto a 100 mesh screen (150$\mu$ openings) and is shaken horizontally and occasionally tapped to allow liquid and crystals of less than 150$\mu$ to pass through. The residue remaining on the screen is washed off the screen with distilled water into a tared dish and then thoroughly dried. The dish containing the retained residue is then reweighed. The difference between the weights of the dry residue-containing dish and the tared dish is a measure of the amount of materials which would tend to plug a spray nozzle.

FORMULATION

The following examples illustrate typical formulations of the invention and the ways in which they can be prepared.

| Formulation A Wettable Powder | |
|---|---|
| 1-Methyl-3-cyclohexyl-6-dimethylamino-s-triazine-2,4(1H,3H)-dione | 66% wt. |
| Diisopropylnaphthalene sulfonate, Na salt | 5% |
| Hydroxypropyl methylcellulose | 2% |
| Granulated sugar | 2% |

-continued

| Formulation A Wettable Powder | |
|---|---|
| Attapulgus clay | 25% |
| | 100% wt. |

The dry ingredients are thoroughly blended and hammermilled to produce a mixture having an average particle size below 200 microns. The wettable powder is then reblended and packaged.

| Formulation B Sprayable Solution | |
|---|---|
| 1-Methyl-3-cyclohexyl-6-dimethylamino-s-triazine-2,4 (1H,3H)-dione | 26% wt. |
| Diisopropylnaphthalene sulfonate, Na salt | 2% |
| Ethanol | 40% |
| Water | 32% |
| | 100% wt. |

The surfactant and triazine are added to the ethanol and dissolved by stirring. The solution is then diluted with water and passed through a 200 mesh screen (U.S.S.) to remove any extraneous material.

| Formulation C Wettable Powder | |
|---|---|
| Formulation A wettable powder | 27% wt. |
| 3-(3,4-Dichlorophenyl)-1,1-dimethylurea crystals | 54% |
| Synthetic fine silica | 5% |
| Kaolinite clay | 14% |
| | 100% wt. |

| Formulation D Low Viscosity Slurry | |
|---|---|
| (a) Formulation of Powder | |
| 1-Methyl-3-cyclohexyl-6-dimethylamino-s-triazine-2,4(1H,3H)-dione | 94% wt. |
| Hydrated sodium silicoaluminate | 3.8% |
| Granulated sugar | 1.0% |
| Hydroxypropyl methyl cellulose | 1.0% |
| Sodium dioctyl sulfosuccinate | 0.2% |
| | 100.0% wt. |

The dry ingredients are thoroughly blended and hammermilled to produce an average particle size under 200 microns. The wettable powder is then reblended.

| (b) Formulation of Slurry | |
|---|---|
| Wettable powder per (a) | 96% wt. |
| Diisopropylnaphthalene sulfonate, Na salt | 4% |
| | 100% wt. |

The sulfonate salt is added to water (about 10° C.) in a concentrate tank. The wettable powder is then added and stirred for a time sufficient to form a concentrated solution 2.5–6.0% wt. The concentrated spray mix can then be used as made or it can be diluted further for spraying.

| Formulation E Sprayable Solution | |
|---|---|
| 1-Methyl-3-cyclohexyl-6-dimethylamino-s-triazine-2,4(1H,3H)-dione | 26% wt. |
| Ethanol | 42% |
| Water | 32% |
| | 100% wt. |

The triazine is added to the ethanol and dissolved by stirring. The solution is then diluted with water and passed through a 200 mesh screen (U.S.S.) to remove any extraneous material.

EXAMPLE 1

A series of screening tests was performed on a large number of candidate materials for changing the crystallization characteristics of spray compositions containing the above-referred triazine compound.

In these screening tests, 1 g of each candidate material was added to 100 g of Formulation E herbicide solution and stirred to complete solution. The solution of herbicide and candidate material was then poured into 300 ml of 5° C. tap water seeded with 1-methyl-3-cyclohexyl-6-dimethylamine-s-triazine-2,4(1H,3H)-dione trihydrate to assure crystallization and stirred for 15 minutes at 300 rpm while maintaining the solution temperature at 5° C. The resultant test solution was then poured onto a 100 mesh U.S.S. screen and the amount of residue larger than 100 mesh (150 microns) which was retained thereon was measured by the procedure described hereinabove. The following materials were tested:

| The following materials were tested: | |
|---|---|
| Granulated sugar | |
| Urea | |
| Glycerine | |
| Low viscosity aromatic oil | Sunspray 7E Oil, Sun Co. Marcus Hook, PA |
| Calcium lignosulfonate | Lignosol BD, Lignasol Chemicals, Quebec, Canada |
| Polyvinyl alcohol | Gelvatol 20/30, Monsanto Co., St. Louis, MO |
| Sorbitan monolaurate | Span 20, Imperial Chemical Industries - US, Wilmington, DE |
| Sorbitan tristearate | Span 65, Imperial Chemical Industries - US, Wilmington, DE |
| Ethylene oxide-propylene glycol addition polymer | Pluronic F-68, Wyandotte Chemicals Co., Wyandotte, MI |
| Polyoxyethylene lauryl ether | Brij 30, Imperial Chemical Industries - US, Wilmington, DE |
| Polyoxyethylene dodecyl ether | Surfactant WK, E. I. du Pont de Nemours and Co. Wilmington, DE |
| Polyoxyethylene sorbitan monopalmitate | Tween 40, Imperial Chemical Industries - US, Wilmington, DE |
| Polyoxyethylene stearate | Myrj 52, Imperial Chemical Industries - US, Wilmington, DE |
| Organophosphate ester | Gafac 510, GAF Corporation, New York, NY |
| Alkylnaphthalene sulfonate, Na salt | Petro Ag Special, Petrochemicals Co. Fort Worth, TX |
| Alkylnaphthalene sulfonate, Na salt | Petro AA, Petrochemicals Co., Fort Worth, TX |
| Mono- and dimethylnaphthalene sulfonate, Na salt | Morwet M, Petrochemicals Co., Fort Worth, TX |
| Butylnaphthalene sulfonate, Na salt | Morwet B, Petrochemicals Co., Fort Worth, TX |
| Mixed diisopropylnaphthalene sulfonate, Na salt | Alkanol XC, E. I. du Pont de Nemours and Co., Wilmington, DE |
| Mixed diisopropylnaphthalene sulfonate, Na salt | Morwet IP, Petrochemicals Co., Fort Worth, TX |
| Diisopropylnaphthalene sulfonate, Na salt | Nekal BA77, GAF Corp., New York, NY |
| Diisopropylnaphthalene | Nekal BA78, GAF Corp., |

-continued

| The following materials were tested: | |
|---|---|
| sulfonate, Na salt | New York, NY |
| Mixed Alkylnaphthalene sulfonate, Na salt | Sellogen HR-90, Diamond Shamrock Chemical Co., Morristown, NJ |
| Mixed Alkylnaphthalene sulfonate, Na salt | Sellogen W, Diamond Shamrock Chemical Co., Morristown, NJ |

All but the last six of the above-listed materials were found to be insufficiently effective or not effective at all in the test procedure in that they exhibited residue retention of 47% wt. or higher. On the other hand, the last six materials, all of which contained isopropyl-substituted naphthalene groups, were found to be at least moderately effective in they they exhibited residue retention of less than 40%. The testing of these materials at a level of 2 g in place of the 1 g concentration used for initial screening resulted in much lower residue retention. For example, the formulation containing 2 g of the mixed diisopropylnaphthalene sulfonate Alkanol ® XC surface active agent (trademark of E. I. du Pont de Nemours and Company, Wilmington, DE) yielded a residue retention of only 0.12% wt.

Of particular interest was the fact that not only were the alkylnaphthalene sulfonates found to be the only materials having significant operability, but only the isopropyl-substituted materials were effective. Both lower and higher alkyl homologs were ineffective.

EXAMPLE 2

In this series of tests, the effect of water temperature variations was observed for spray formulations containing various amounts of surfactant. In these tests, 13 g of Formulation D(a) wettable powder was admixed into 100 ml of water at the indicated temperature in accordance with the above-described test procedure. The results were as follows:

TABLE 1

| | Surfactant | | | Retained |
|---|---|---|---|---|
| Test No. | Identity | Amount (% wt.)* | Water Temperature (°C.) | Residue (% wt.)* |
| 1 | — | none | 5 | 75 |
| 2 | — | none | 10 | 68 |
| 3 | — | none | 15 | 85 |
| 4 | Alkanol XC | 2 | 5 | 2.0 |
| 5 | Alkanol XC | 4 | 5 | 1.8 |
| 6 | Alkanol XC | 4 | 10 | 1.5 |
| 7 | Alkanol XC | 8 | 10 | 1.0 |
| 8 | Nekal BA77 | 8 | 5 | 1.2 |
| 9 | Nekal BA77 | 8 | 15 | 1.0 |

*Basis dry triazine compound

The foregoing data in Table 1 show only a minor effect of temperature on the amount of retained crystals at 5°-15° C. However, the addition of as little as 2% wt. surfactant reduced crystal retention to as little as 2.7% of the amount retained in the aqueous spray containing no surfactant. These data also reveal a modest advantage to adding even higher amounts of surfactant once a threshold concentration is added.

EXAMPLE 3

In this series of tests, the effects of water temperature, dilution and surfactant concentrations were studied. In these tests, 100 ml of Formulation E sprayable solution was admixed with the indicated amount of solid surfactant and the resulting admixture was diluted with the indicated amount of water at the specified temperature in accordance with the above-described test procedure. The results were as follows:

Table 2

| | Surfactant | | Water | | |
|---|---|---|---|---|---|
| Test No. | Identity | Amount (% wt.)* | Amount (ml) | Temperature (°C.) | Retained Residue (% wt.)* |
| 10 | — | none | 100 | 5 | 83 |
| 11 | — | none | 500 | 5 | 51 |
| 12 | — | none | 100 | 10 | 58 |
| 13 | — | none | 500 | 10 | 42 |
| 14 | — | none | 300 | 5 | 60 |
| 15 | Alkanol XC | 2 | 300 | 5 | 54 |
| 16 | Alkanol XC | 6 | 300 | 5 | 31 |
| 17 | Alkanol XC | 10 | 300 | 5 | 0.3 |
| 18 | Nekal BX78 | 2 | 500 | 15 | 0.4 |
| 19 | Nekal BA77 | 2 | 500 | 15 | 0.5 |
| 20 | Sellogen W | 8 | 500 | 15 | 0.5 |

*Basis dry triazine compound

The above data show, as expected, that greater dilution does decrease the crystallization problem. However, an order of magnitude improvement is more readily obtained by the addition of an alkali metal isopropyl-substituted naphthalene sulfonate.

EXAMPLE 4

In this series of tests, it is shown that the addition of diisopropylnaphthalene sulfonate to inhibit the formation of large crystals is effective in quite hard water, i.e., 840 ppm hardness. In these tests, 13 g of Formulation D(a) wettable powder was admixed into 100 ml of water at the indicated temperature in accordance with the above-described test procedure. The results are given in Table 3, below:

Table 3

| | Surfactant | | Water | Retained |
|---|---|---|---|---|
| Test No. | Identity | Amount (% wt.)* | Temperature (°C.) | Residue (% wt.)* |
| 21 | — | none | 5 | 86 |
| 22 | — | none | 10 | 83 |
| 23 | — | none | 15 | 84 |
| 24 | — | none | 25 | 1.2 |
| 25 | Alkanol XC | 4 | 5 | 1.4 |
| 26 | Alkanol XC | 4 | 10 | 1.4 |
| 27 | Alkanol XC | 4 | 15 | 0.9 |
| 28 | Alkanol XC | 4 | 25 | 1.2 |

*Basis dry triazine compound

These data show quite graphically that water hardness does not interfere with the ability of the surfactant to alter the crystallization behavior of the system favorably. Of particular interest is the fact that, to obtain a similar degree of crystal inhibition, it would be necessary to maintain the formulation in the field at 25° C. or higher.

EXAMPLE 5

In this series of tests, it is shown that the typical variation in pH, which might be experienced in using different sources of water for formulation, likewise do not significantly interfere with the ability of the surfactant to alter the crystallization characteristics of the system advantageously. In these tests, 13 g of Formulation D wettable powder and 4% wt. Alkanol ® XC were admixed with 300 ml of water having a pH as indicated. The results are given in Table 4 below:

Table 4

| Test No. | Water Temperature (°C.) | pH | Retained Residue (% wt.) |
| --- | --- | --- | --- |
| 29 | 5 | 5.1 | 0.5 |
| 30 | 10 | 5.1 | 0.5 |
| 31 | 15 | 5.1 | 0.4 |
| 32 | 25 | 5.1 | 0.6 |
| 33 | 5 | 9.0 | 1.2 |
| 34 | 10 | 9.0 | 1.1 |
| 35 | 15 | 9.0 | 1.2 |
| 36 | 25 | 9.0 | 1.3 |

We claim:

1. A water-dispersible triazine herbicide composition, having improved crystallization characteristics when dispersed in water below about 37° C. at concentrations above the solubility limit of the triazine, consisting essentially of (a) 1-methyl-3-cyclohexyl-6-dimethylamino-s-triazine-2,4(1H,3H)-dione and (b) at least about 2% by weight, basis dry triazine, of a surfactant selected from the group consisting of isopropyl naphthalene sulfonic acid and alkali metal or alkaline earth metal salts thereof.

2. The composition of claim 1 comprising an admixture of finely divided particles of the triazine compound and of the surfactant.

3. The composition of claim 1 comprising finely divided particles of the triazine herbicide having the surfactant incorporated therein.

4. The composition of claim 1 comprising finely divided particles of the triazine herbicide having the surfactant coated on the surface thereof.

5. The composition of claim 1 comprising a dispersion of the triazine herbicide in an aqueous solution of the surfactant.

6. The composition of claim 5 in which the dispersion is a flowable slurry.

7. The composition of claim 5 in which triazine herbicide is dissolved in the aqueous solution of surfactant.

8. The composition of claim 1 in which the surfactant is present in the amount of at least about 5% by weight, basis dry triazine.

9. The composition of claim 1 in which the surfactant contains an average of about 2.5 isopropyl groups per molecule of naphthalene sulfonate.

10. The composition of claim 8 in which the surfactant contains an average of about 2.5 isopropyl groups per molecule of naphthalene sulfonate.

11. A sprayable herbicide composition comprising the composition of claim 1 dispersed in water below about 37° C. at a concentration between the solubility limit and about 12% by weight of the triazine.

12. The method of controlling the growth, below a temperature of about 37° C., of crystals of 1-methyl-3-cyclohexyl-6-dimethylamino-s-triazine-2,4(1H,3H)-dione from aqueous solutions in which the triazine compound is dispersed at a concentration in excess of its solubility comprising incorporating into the solution at least about 2% by weight, basis dry triazine, of an isopropyl naphthalene sulfonic acid surfactant or alkali metal or alkaline earth metal salt thereof.

* * * * *